(12) United States Patent
Nachum

(10) Patent No.: US 6,792,313 B2
(45) Date of Patent: Sep. 14, 2004

(54) MUSCLE STIMULATION IN A CAST IMMOBILIZED LIMO

(75) Inventor: Zvi Nachum, Tiberias (IL)

(73) Assignee: Stimu-Heal Inc

( * ) Notice: Subject to any disclaimer, the term of this patent is extended or adjusted under 35 U.S.C. 154(b) by 0 days.

(21) Appl. No.: 10/108,436

(22) Filed: Mar. 29, 2002

(65) Prior Publication Data

US 2003/0220672 A1 Nov. 27, 2003

(51) Int. Cl.$^7$ .............................................. A61N 1/32
(52) U.S. Cl. ....................................................... 607/48
(58) Field of Search .............................. 602/48, 50, 72, 602/74; 607/49, 51, 52, 58, 1, 2, 66, 68, 70, 71, 73

(56) References Cited

U.S. PATENT DOCUMENTS

| | | | |
|---|---|---|---|
| 4,535,775 A | 8/1985 | Brighton et al. | |
| RE32,091 E | * 3/1986 | Stanton | 607/48 |
| 4,574,809 A | 3/1986 | Talish et al. | |
| 4,998,532 A | 3/1991 | Griffith | |
| 6,061,597 A | 5/2000 | Rieman et al. | |
| 6,273,864 B1 | 8/2001 | Duarte et al. | |
| 6,321,119 B1 | 11/2001 | Kronberg | |
| 2002/0016618 A1 | * 2/2002 | Da Silva et al. | 607/72 |

* cited by examiner

Primary Examiner—George R. Evanisko
(74) Attorney, Agent, or Firm—Mark M. Friedman

(57) ABSTRACT

A method of electrically stimulating muscles in a cast-bearing limb so as to inhibit muscle atrophy, the method including the steps of: (a) providing a system including: (i) at least two electrodes; (ii) a signal generator operatively connected to the electrodes, and (iii) a power source providing power to the signal generator; (b) situating the electrodes in contact with tissue on the cast-bearing limb; (c) stimulating the muscles by externally inducing a percutaneous flow of electrical current between the electrodes through the tissue by establishing a plurality of external bipolar voltage waves across the electrodes, the plurality of bipolar voltage waves defining a treatment period, and (d) applying, over a 24-hour period, at least 12 distinct treatment periods.

34 Claims, 4 Drawing Sheets

MUSCLE STIMULATION IN A CAST IMMOBILIZED LIMO

FIELD AND BACKGROUND OF THE INVENTION

The present invention relates to muscle stimulation using electrical impulses and, in particular, to a method of stimulating muscles in a cast-immobilized limb as a means of inhibiting muscle atrophy.

For bone fractures of different kinds, conventional medical treatment includes the immobilization of the portions of the body proximate the injury. This is often accomplished by using a cast, which is the simplest and crudest method of protecting an injury. The cast allows virtually no movement at all and is widely used to insure against reinjury. The impairment of movement is of particular importance in the repair and/or union of bone fractures.

Unfortunately, this method of protecting the injury often does not provide adequate means for exercising the body portions proximate the injury. For instance, a cast is often not strong enough, without additional reinforcement, to permit isometric exercising.

It is known that both muscles and bones should be exercised to prevent atrophy and maintain strength. When an individual sustains a physical injury which involves damage to bones, muscle tissue, connective tissue or the like, it is usually highly desirable for the muscle in the vicinity of the injury to be exercised in a controlled manner within specific parameters wherein the injured bone and/or tissue will remain stable. Unfortunately, however, the physician is generally unable to obtain adequate information or assurances about the manner in which a particular patient will conduct prescribed exercise. The physician does not know how much stress the patient can or will exert voluntarily, and does not know how well the patient will adhere to a schedule of repetitive exercise events. Unsupervised exercise is likely to deleteriously affect the injured tissues, thereby increasing the healing time, and sometimes causing irreparable damage. Furthermore, in most instances, the severity of the injury coupled with the rigidity of the cast render impossible the exercise of the muscles disposed thereunder.

One promising direction is to activate the affected muscles using electrical stimulation. There exist several devices for electrical stimulation of injured tissue situated underneath a cast. U.S. Pat. No. 4,574,809 to Talish, et al., entitled: "Portable Non-Invasive Electromagnetic Therapy Equipment", teaches a cast-embeddable coil structure which includes a single connector fitting, designed for exposure externally of a completed cast and for removable mounting and electrical connection to a self-contained light-weight rechargeable portable signal-generator unit. The signal-generator unit is mounted to the cast only for periods of therapeutic treatment, and is removably mounted to a less-portable charging unit in intervals between periods of therapeutic treatment.

U.S. Pat. No. 4,998,532 to Griffith, entitled "Portable Electro-Therapy System", teaches a portable non-invasive apparatus for electro-therapeutic stimulation of tissue and bone healing readily worn or carried by a patient, capable of generating an energy-efficient signal co-acting with a suitable transducer of the signal, thereby realizing portability and stimulating tissue and bone healing. The teachings of the above-mentioned applications relate primarily to the stimulation of bone healing.

U.S. Pat. No. 6,321,119 to Kronberg, entitled "Pulsed Signal Generator For Bioelectric Stimulation And Healing Acceleration", teaches a pulsed signal generator for biomedical applications, including electrical stimulation of fracture healing, treatment of osteoporosis, strengthening of freshly-healed bone after removal of a cast or other fixation device, and iontophoresis. The generator includes dual asymmetric oscillators and associated circuitry to deliver signals efficiently throughout the area to be treated. The components of the generator are selected so as to produce any desired output signal, including fixed and variable amplitude, fixed, variable, and swept frequency signals, and DC biasing.

Although the teachings of U.S. Pat. No. 6,321,119 are directed primarily to bone healing and pain reduction (similar to TENS), it is noted that electrical stimulation can also produce a wide range of responses in other body systems, that the frequency and timing of the signal waveform appear to have some bearing on which body systems are more affected.

It is further noted that

"it appears possible that appropriately-designed waveforms may prove useful for stimulating muscles, such as those in fractured and immobilized limbs or those of temporarily paralyzed persons, to help prevent atrophy and preserve muscle tone. Other applications may include stimulation of the endocrine glands and the immune system. For example, autoimmune conditions such as arthritis may be susceptible to localized, bioelectric immunosuppression without affecting the ability of the body as a whole to throw off infection. Much more research will be needed in order to evaluate the potential of such effects in healing or in the treatment of diseases, and to determine the optimum waveform for each application."

Thus, though is evident from U.S. Pat. No. 6,321,119 to Kronberg that appropriately-designed waveforms for stimulating muscles would be desirable, there is no practical instruction regarding the specific nature of the waveform, nor regarding the treatment procedure.

U.S. patent application No. 20020016618 to Da Silva, et al., entitled: "Integrated Cast And Muscle Stimulation System", teaches a device that allows electrical stimulation to an anatomical site that is covered by a cast. The electrode is applied to achieve a desired physiological response (e.g., bone growth), treatment of pain, or the prevention of muscle atrophy.

It is further disclosed that:

"in normal use, the electrode module would only be used continuously for the first few days to block or reduce pain. After that time, electrode modules would only be applied several times a day for 10–20 minutes to stimulate the muscles and reduce muscular atrophy. Initially, the intensity of muscle stimulation would be low in order to prevent putting too much stress on the fracture. As the fracture heals, stimulation is increased to ensure that muscle tone is maintained during the one to three month healing period. The electrical stimulation unit can be preprogrammed to deliver a physician prescribed intensity pattern throughout the entire healing period.

Like U.S. Pat. No. 6,321,119 to Kronberg, U.S. patent application No. 20020016618 to Da Silva, et al., does not provide practical instruction regarding specific wave forms, patterns, and intensities for effective stimulation of cast-immobilized muscles. With regard to a treatment procedure, it is generally stated that electrically-induced stimulation of the affected muscle tissue should be applied several times a day for 10–20 minutes, in order to reduce muscular atrophy.

In the absence of practical direction with regard to effective stimulation of cast-impaired or cast-immobilized muscles, it would be highly advantageous to have a method for preventing muscular atrophy of such muscles, using electrical stimulation. It would be of further benefit for this method to be painless and convenient to apply. Finally, it would be highly advantageous to have a method that is applied by the patient in a safe, reliable, and effective manner, such that substantially no professional supervision is required, and can be effected automatically, without any special attention on the part of the patient.

SUMMARY OF THE INVENTION

The present invention is a safe, effective, and reliable method of stimulating muscles in a cast-immobilized limb in order to inhibit muscle atrophy.

According to the teachings of the present invention there is provided, a method of electrically stimulating muscles in a cast-bearing limb so as to inhibit muscle atrophy, the method including the steps of: (a) providing a system including: (i) at least two electrodes; (ii) a signal generator operatively connected to the electrodes, and (iii) a power source providing power to the signal generator; (b) situating the electrodes in contact with tissue on the cast-bearing limb; (c) stimulating the muscles by externally inducing a percutaneous flow of electrical current between the electrodes through the tissue by establishing a plurality of external bipolar voltage waves across the electrodes, the plurality of bipolar voltage waves defining a treatment period, and (d) applying, over a 24-hour period, at least 12 distinct treatment periods.

According to further features in the described preferred embodiments, the treatment periods are administered during at least 10 hours of a 24-hour period, more preferably, during at least 16 hours of a 24-hour period, and most preferably, during at least 24 hours of a 24-hour period.

According to further features in the described preferred embodiments, the treatment periods are separated by rest periods having zero voltage applied between the electrodes, and wherein each of the rest periods is less than 12 hours.

According to further features in the described preferred embodiments, each of the rest periods is less than 6 hours, and most preferably less than 1 hour.

According to further features in the described preferred embodiments, the bipolar voltage waves have a frequency of less than 20 Hz, preferably less than 5 Hz. Most preferably, the voltage waves have a frequency in a range of 0.5–2.5 Hz.

According to further features in the described preferred embodiments, the treatment periods have a duration of less than 300 seconds.

According to further features in the described preferred embodiments, the treatment periods have a duration of less than 180 seconds.

According to further features in the described preferred embodiments, the treatment periods have a duration in a range of 30–120 seconds.

According to further features in the described preferred embodiments, the treatment periods are applied 4–20 times per hour.

According to further features in the described preferred embodiments, the treatment periods are applied 8–16 times per hour.

According to further features in the described preferred embodiments, the bipolar voltage waves have a varying frequency.

According to further features in the described preferred embodiments, the bipolar voltage waves have a frequency varying between 0.5–2.5 Hz.

According to further features in the described preferred embodiments, the bipolar voltage waves have a frequency varying by a factor of 1.2–4.0.

According to further features in the described preferred embodiments, the bipolar voltage waves have a frequency varying by a factor of 1.5–2.5.

According to further features in the described preferred embodiments, the ratio defined by a length of said treatment period divided by a length of one of said rest periods is less than 0.5, preferably less than 0.3, and most preferably in the range of 0.1–0.25.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
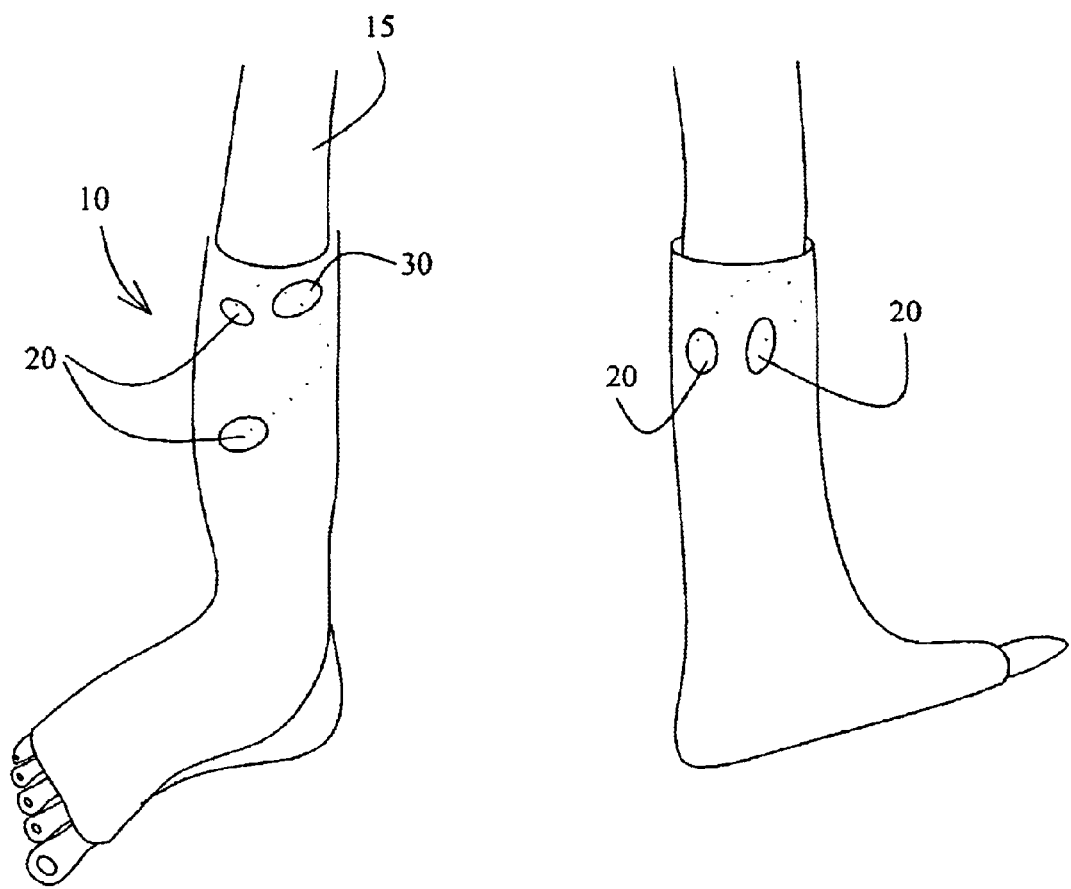
FIG. 1 shows a leg with a cast having an integrated muscle stimulation system, as disclosed in U.S. patent application No. 20020016618 to Da Silva, et al.

The present invention is a safe, effective, and reliable method of electrically stimulating muscles in a cast-impaired or cast-immobilized limb so as to inhibit muscle atrophy.

The principles and operation of the electrical stimulation method according to the present invention may be better understood with reference to the drawings and the accompanying description.

Before explaining at least one embodiment of the invention in detail, it is to be understood that the invention is not limited in its application to the details of construction and the arrangement of the components set forth in the following description or illustrated in the drawing. The invention is capable of other embodiments or of being practiced or carried out in various ways. Also, it is to be understood that the phraseology and terminology employed herein is for the purpose of description and should not be regarded as limiting.

The inventive method can be applied using various known devices. An illustration of one exemplary device, described in U.S. patent application No. 20020016618 to Da Silva, et al., is provided in FIG. 1. FIG. 1 shows the key components of the integrated cast and muscle stimulation device, as it would be used for a lower leg fracture. The cast 10 is molded around the lower leg 15 to immobilize the fracture. Replaceable electrodes 20 are positioned over superficial aspects of the peripheral nerves innervating the musculature surrounding the fracture site. An electrical stimulation unit 30 applies voltage pulses to the electrodes through buried electrical conductors (not shown).

The above-described electrical stimulation unit is similar to a stimulation unit disclosed in U.S. Pat. No. 4,398,545, which is incorporated by reference for all purposes, as if fully set forth herein.

Figure 2:
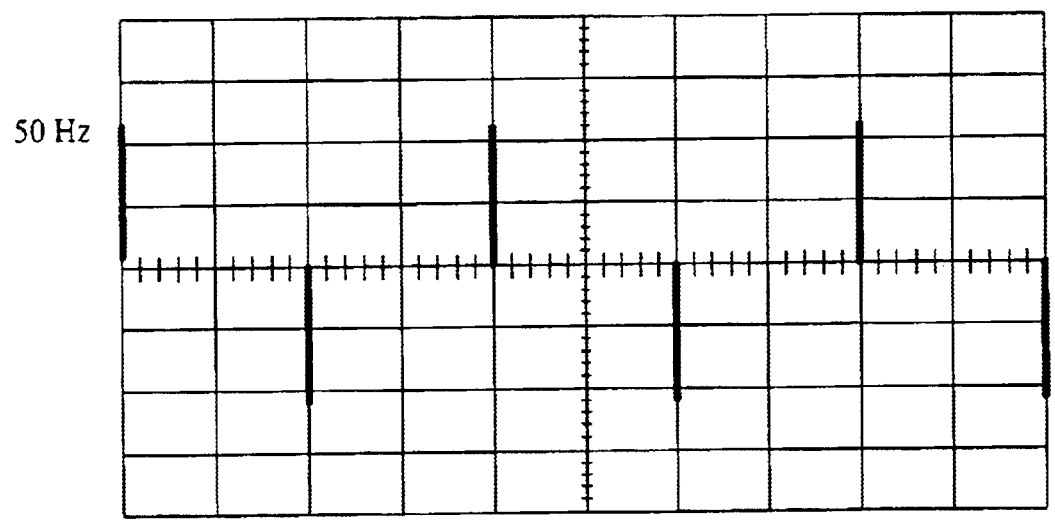
FIG. 2 illustrates a typical chart recording of an electrical signal used in TENS (transcutaneous electrical nerve stimulation) therapy.

FIG. 2 illustrates a typical electrical signal used in TENS (transcutaneous electrical nerve stimulation) therapy. The frequency of the monopolar wave form is 50 Hz; the peak voltage is approximately 18 Volts. Such voltage forms are typically used in suppressing pain and, to a lesser degree, in muscle rehabilitation.

By sharp contrast, the treatment method of the present invention is directed neither towards pain suppression nor to muscle rehabilitation. The present invention substantially reduces or eliminates the need for muscle rehabilitation by maintaining muscle function in the area of (and surrounding) the injury. Instead of applying electrode modules "several times a day for 10–20 minutes to stimulate the muscles and reduce muscular atrophy", as suggested in U.S. patent application No. 20020016618, I have discovered that it is significantly more effective to stimulate the affected muscles frequently and for short durations.

In the inventive treatment method, the application of the electrical treatment to the affected muscles is effected at least twice per hour. It is highly desirable to intermittently apply the electrical treatment 24 hours per day, over the entire course of the limb impairment or immobilization.

More preferably, the electrical treatment method is effected 4–20 times per hour, most preferably 8–16 times per hour. On a per day basis, the method is effected at least 40 times, more preferably 100–500 times, and most preferably 200–400 times.

The duration of each application is preferably between 15–180 seconds and more preferably, between 30–120 seconds. Assuming a treatment rate of 16 times per hour and a duration of 30 seconds (½ minute) for each application, we calculate 8 minutes of treatment per hour, and 52 minutes of rest, corresponding to 16 alternate periods of 0.5 minute application (including electrical stimulation) and 3.25 minutes rest. Assuming a treatment rate of 16 times per hour and a duration of 120 seconds (2 minutes) for each application, we calculate 32 minutes of treatment per hour, and 28 minutes of rest, corresponding to 16 alternate periods of 2 minute application and 1.75 minutes rest. Similarly, assuming a treatment rate of 8 times per hour and a duration of 30 seconds (½ minute) for each application, we calculate 4 minutes of treatment per hour, and 56 minutes of rest, corresponding to 8 alternate periods of 0.5 minute application and 7 minutes rest.

Voluntary contraction and relaxation of limb muscles is performed extremely frequently by the healthy individual, even during sleep. When a limb has been immobilized by a cast or the like, the muscles in the affected area become substantially inactive, which over the course of the immobilization, leads to reduced blood flow, muscular atrophy, and reduced flexibility. In the method of the present invention, voltage wave forms are utilized to artificially effect contraction of the muscles in a relatively frequent fashion, such that the muscles maintain a substantially normal level of activity. This obviates the need for physical therapy after removal of the cast, as well as known electrical stimulation procedures for rehabilitating the muscle tissue.

Figure 3A:
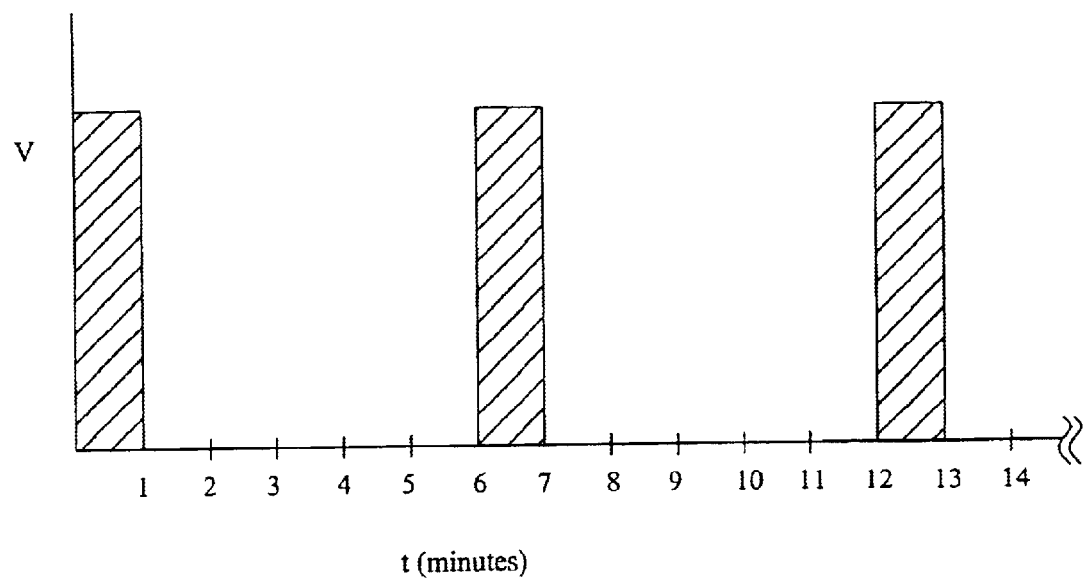
FIG. 3a is an exemplary graph of the electrical treatment method, showing peak voltage vs. time, is provided in FIG. 3a. Over the first minute plotted on the graph, electricity is applied to the affected area of tissue. Following this period of stimulation, the muscle is allowed to rest.
Figure 3B:
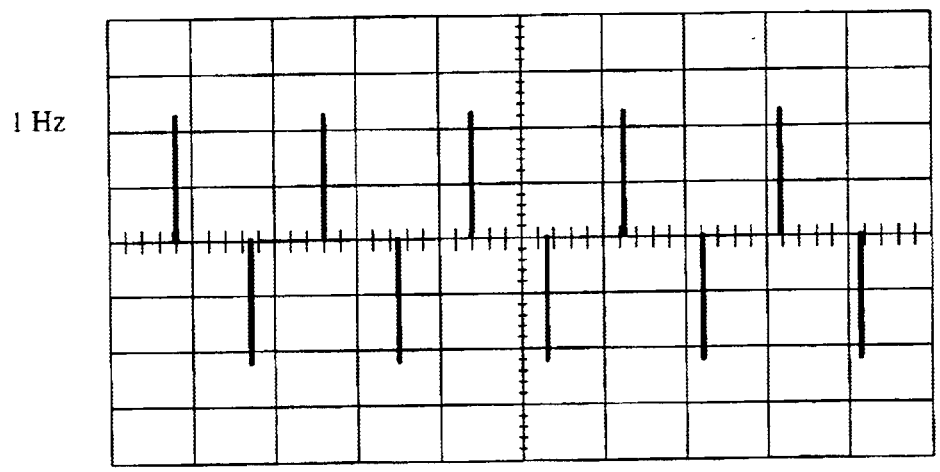
FIG. 3b illustrates a typical chart recording of an electrical signal applied during the period of stimulation, in accordance with the present invention.

During the above-described period of stimulation (one minute, in the example provided in FIG. 3a), the electrical stimulation is preferably applied at a frequency below 20 Hz, more preferably at a frequency in the range of 0.25–5 Hz, and most preferably, at a frequency in the range of 0.5–2.5 Hz. The frequency values refer to a cycle consisting of a bipolar wave form. An exemplary voltage wave pattern for the period of stimulation, having a frequency of 1 Hz, is provided in FIG. 3b.

Figure 4:
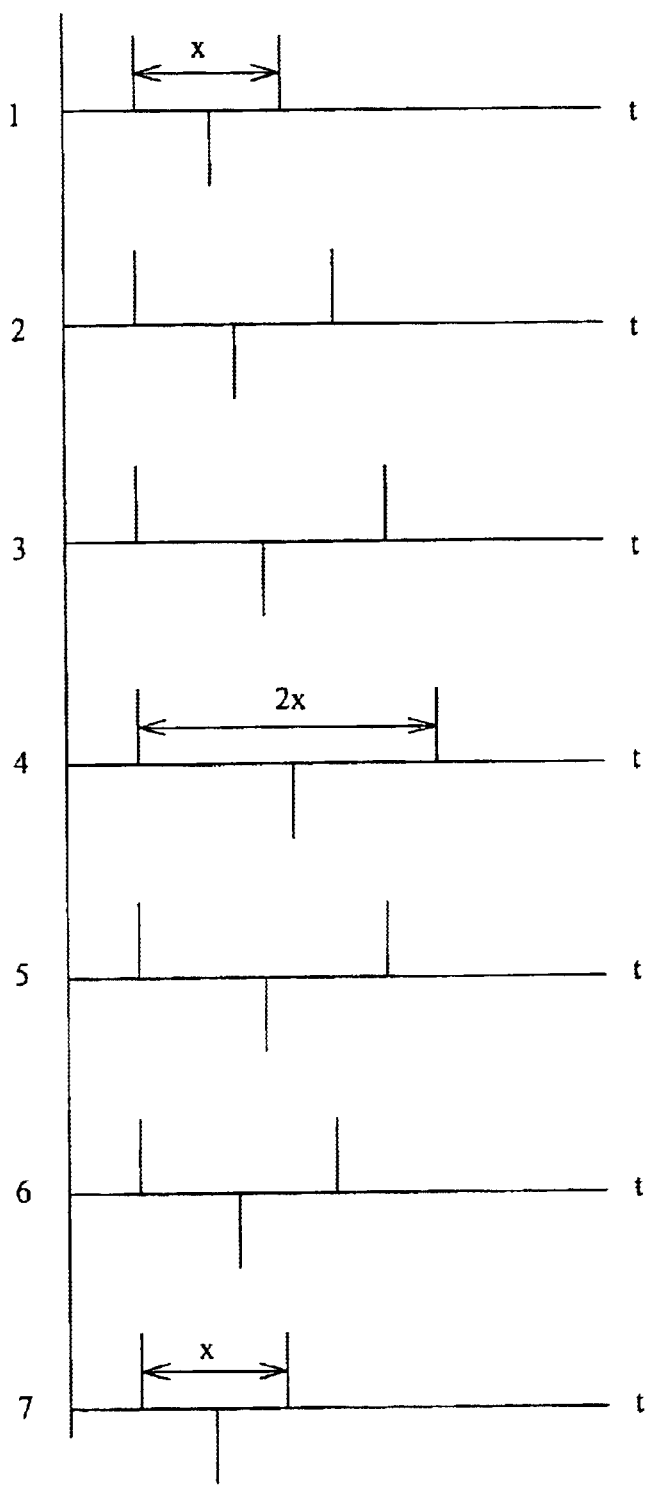
FIG. 4 is a schematic multiple plot of voltage vs. time for a signal having a varying frequency, in accordance with a preferred embodiment of the present invention.

Although a constant frequency has been found to be effective, it has been discovered that by varying the frequency during each period of stimulation in a particular manner, the efficacy of the treatment is appreciably improved. FIG. 4 is a multiple plot of voltage vs. time illustrating a signal in which the frequency varies with time. In stage 1, the frequency of the bipolar wave is 1/X. Over time, as shown in stages 2–4, the frequency of the bipolar wave form decreases to a minimum of 1/(2X) in stage 4. Subsequently, the frequency of the bipolar wave form increases, returning to the initial frequency of 1/X in stage 7. Such a pattern is preferably repeated at least twice over the course of a treatment period (i.e., 1 minute in the example provided in FIG. 3a).

Without wishing to be limited by theory, I attribute the superior performance of the varying frequency stimulation treatment to the activation of a much broader area of muscle tissue, relative to the stimulation treatment having a wave form of constant frequency.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of inhibiting muscle atrophy in an at least partially-immobilized limb by electrically stimulating muscles, the method comprising the steps of:
   (a) providing a system including:
      (i) at least two electrodes;
      (ii) a signal generator operatively connected to said electrodes, and
      (iii) a power source providing power to said signal generator;
   (b) situating said electrodes in contact with tissue on the limb;

(c) stimulating the muscles by externally inducing a percutaneous flow of electrical current between said electrodes through said tissue by establishing a plurality of external voltage waves across said electrodes using said signal generator, said plurality of bipolar voltage waves defining a single treatment period, and (d) applying at least 12 distinct treatment periods over at least 10 hours of a 24-hour period.

2. The method of claim 1, wherein said external voltage waves are external bipolar voltage waves.

3. The method of claim 1, wherein said at least 10 hours of a 24-hour period is at least 16 hours.

4. The method of claim 1, wherein said at least 10 hours of a 24-hour period is substantially 24 hours.

5. The method of claim 1, wherein said treatment periods are separated by rest periods having substantially zero voltage applied between said electrodes, and wherein each of said rest periods is less than 12 hours and more than 7 minutes.

6. The method of claim 5, wherein each of said rest periods is less than 6 hours and more than 5 minutes.

7. The method of claim 5, wherein each of said rest periods is less than 1 hour and more than 3.25 minutes.

8. The method of claim 5, wherein each of said rest periods is less than 1 hour and more than 1.75 minutes.

9. The method of claim 2, wherein said bipolar voltage waves have a frequency of less than 5 Hz.

10. The method of claim 2, wherein said bipolar voltage waves have a frequency in a range of 0.5–2.5 Hz.

11. The method of claim 1, wherein said treatment periods have a duration of less than 300 seconds.

12. The method of claim 1, wherein said treatment periods have a duration of less than 180 seconds.

13. The method of claim 1, wherein said treatment periods have a duration in a range of 30–120 seconds.

14. The method of claim 1, wherein said treatment periods are applied 4–20 times per hour over said at least 10 hours of said 24-hour period.

15. The method of claim 1, wherein said treatment periods are applied 8–16 times per hour over said at least 10 hours of said 24-hour period.

16. The method of claim 1, wherein said voltage waves have a varying frequency.

17. The method of claim 16, wherein said voltage waves have a frequency varying between 0.5–2.5 Hz.

18. The method of claim 16, wherein said voltage waves have a frequency varying by a factor of 1.2–4.0.

19. The method of claim 18, wherein said voltage waves have a frequency varying by a factor of 1.5–2.5.

20. The method of claim 18, wherein a ratio defined by a length of said treatment period divided by a length of one of said rest periods is less than 0.25.

21. The method of claim 1, wherein said treatment periods are applied at least 100 times during said at least 10 hours of said 24-hour period.

22. The method of claim 1, wherein said treatment periods are applied at least 200 times during said at least 10 hours of said 24-hour period.

23. The method of claim 1, wherein the at least partially-immobilized limb is a cast-bearing limb.

24. The method of claim 23, wherein said at least 10 hours of a 24-hour period is at least 16 hours.

25. The method of claim 23, wherein a rest period between at least two of said treatment periods is less than 12 hours and more than 5 minutes.

26. The method of claim 25, wherein said rest period is less than 6 hours and more than 3.25 minutes.

27. The method of claim 25, wherein said rest period is less than 1 hour and more than 1.75 minutes.

28. The method of claim 23, wherein said treatment periods are applied 4–20 times per hour over said at least 10 hours of said 24-hour period.

29. The method of claim 23, wherein said treatment periods are applied 8–16 times per hour over said at least 10 hours of said 24-hour period.

30. The method of claim 23, wherein said voltage waves have a varying frequency.

31. The method of claim 23, wherein said voltage waves have a frequency varying between 0.5–2.5 Hz.

32. The method of claim 23, wherein said voltage waves have a frequency varying by a factor of 1.2–4.0.

33. The method of claim 23, wherein said treatment periods are applied at least 100 times during said at least 10 hours of said 24-hour period.

34. The method of claim 23, wherein said treatment periods are applied at least 200 times during said at least 10 hours of said 24-hour period.

* * * * *